United States Patent
Harris, Jr.

(10) Patent No.: US 7,247,158 B2
(45) Date of Patent: Jul. 24, 2007

(54) ACETABULAR IMPACTOR

(75) Inventor: Brian R. Harris, Jr., Cordova, TN (US)

(73) Assignee: Wright Medical Technology, Inc., Arlington, TN (US)

( * ) Notice: Subject to any disclaimer, the term of this patent is extended or adjusted under 35 U.S.C. 154(b) by 439 days.

(21) Appl. No.: 10/704,038

(22) Filed: Nov. 7, 2003

(65) Prior Publication Data
US 2004/0153063 A1  Aug. 5, 2004

Related U.S. Application Data

(60) Provisional application No. 60/444,689, filed on Feb. 4, 2003.

(51) Int. Cl.
*A61B 17/00* (2006.01)

(52) U.S. Cl. ...................... 606/81

(58) Field of Classification Search .......... 606/81, 606/91, 99, 100; 623/22.21–39
See application file for complete search history.

(56) References Cited

U.S. PATENT DOCUMENTS

| | | | |
|---|---|---|---|
| 2,437,014 A * | 3/1948 | Arnesen et al. ............ 340/979 |
| 3,685,058 A | 8/1972 | Tronzo | |
| 3,859,992 A | 1/1975 | Amstutz | |
| 3,874,003 A | 4/1975 | Moser et al. | |
| 4,305,394 A | 12/1981 | Bertuch, Jr. | |
| 4,399,813 A | 8/1983 | Barber | |
| 4,475,549 A | 10/1984 | Oh | |
| 4,528,980 A | 7/1985 | Kenna | |
| 4,611,587 A * | 9/1986 | Powlan .................. 606/81 |
| 4,632,111 A | 12/1986 | Roche | |
| 4,662,891 A | 5/1987 | Noiles | |
| 4,677,972 A | 7/1987 | Tornier | |
| 4,716,894 A | 1/1988 | Lazzeri et al. | |
| 4,878,918 A | 11/1989 | Tari et al. | |
| 4,994,064 A | 2/1991 | Aboczky | |
| 5,030,221 A | 7/1991 | Buechel et al. | |
| 5,037,424 A | 8/1991 | Aboczsky | |
| 5,061,270 A | 10/1991 | Aboczky | |
| 5,098,437 A | 3/1992 | Kashuba et al. | |
| 5,108,448 A | 4/1992 | Gautier | |
| 5,108,452 A | 4/1992 | Fallin | |
| 5,116,339 A | 5/1992 | Glock | |

(Continued)

FOREIGN PATENT DOCUMENTS

EP  0147339 A2  7/1985

(Continued)

OTHER PUBLICATIONS

Author unknown. Short External Rotator Muscles of the Hip. From www.biyee.net/running/injury/short_rotators.html (2002).

(Continued)

*Primary Examiner*—Eduardo C. Robert
*Assistant Examiner*—James L. Swiger

(57) ABSTRACT

An improved acetabular impactor, especially suitable for use in minimally invasive hip surgeries, is disclosed. The impactor is simple in design and operation and spatially optimized. In particular, the impactor is designed to remotely detach the acetabular shell from the impactor using one handed operation and have the capability to be used with different sized acetabular shells.

18 Claims, 4 Drawing Sheets

U.S. PATENT DOCUMENTS

| | | | |
|---|---|---|---|
| D331,461 S | 12/1992 | Lester | |
| 5,169,399 A | 12/1992 | Ryland et al. | |
| 5,171,243 A * | 12/1992 | Kashuba et al. | 606/86 |
| 5,171,313 A | 12/1992 | Salyer | |
| 5,190,422 A | 3/1993 | Lechot | |
| 5,217,499 A | 6/1993 | Shelley | |
| 5,250,051 A | 10/1993 | Maryan | |
| 5,261,915 A | 11/1993 | Durlacher et al. | |
| 5,284,483 A | 2/1994 | Johnson et al. | |
| 5,320,625 A | 6/1994 | Bertin | |
| 5,344,461 A | 9/1994 | Philpot | |
| 5,364,403 A | 11/1994 | Petersen et al. | |
| 5,417,696 A | 5/1995 | Kashuba | |
| 5,458,637 A | 10/1995 | Hayes | |
| 5,474,560 A | 12/1995 | Rohr, Jr. | |
| 5,486,181 A | 1/1996 | Cohen et al. | |
| 5,499,985 A | 3/1996 | Hein et al. | |
| 5,507,748 A | 4/1996 | Sheehan et al. | |
| 5,540,697 A * | 7/1996 | Rehmann et al. | 606/91 |
| 5,571,111 A * | 11/1996 | Aboczky | 606/91 |
| 5,584,837 A | 12/1996 | Petersen | |
| 5,658,290 A | 8/1997 | Lechot | |
| 5,683,399 A * | 11/1997 | Jones | 606/91 |
| 5,732,992 A * | 3/1998 | Mauldin | 294/119.1 |
| 5,904,688 A | 5/1999 | Gilbert | |
| 5,928,287 A | 7/1999 | Keller | |
| 5,968,049 A | 10/1999 | DaRold | |
| 6,063,123 A | 5/2000 | Burrows et al. | |
| 6,063,124 A * | 5/2000 | Amstutz | 623/22.21 |
| 6,106,536 A | 8/2000 | Lechot | |
| 6,129,732 A | 10/2000 | Lechot | |
| 6,132,469 A | 10/2000 | Schroeder | |
| 6,264,647 B1 | 7/2001 | Lechot | |
| 6,482,209 B1 | 11/2002 | Engh et al. | |
| 6,506,000 B2 | 1/2003 | Lechot | |
| 6,869,903 B2 | 3/2003 | Mears et al. | |
| 6,540,739 B2 | 4/2003 | Lechot | |
| 6,589,285 B2 | 7/2003 | Penenberg | |
| 6,626,913 B1 | 9/2003 | McKinnon et al. | |
| 6,695,850 B2 | 2/2004 | Diaz | |
| 6,702,819 B2 | 3/2004 | Lechot | |
| 6,723,102 B2 | 4/2004 | Johnson et al. | |
| 6,951,563 B2 | 10/2005 | Wolford | |
| 6,953,480 B2 | 10/2005 | Mears et al. | |
| 7,004,946 B2 | 2/2006 | Parker et al. | |
| 7,037,310 B2 | 5/2006 | Murphy | |
| 2003/0004513 A1 | 1/2003 | Guzman et al. | |
| 2003/0220696 A1 | 11/2003 | Mears et al. | |
| 2003/0229352 A1 | 12/2003 | Penenberg | |
| 2003/0229356 A1 | 12/2003 | Dye | |
| 2003/0229357 A1 | 12/2003 | Dye | |

FOREIGN PATENT DOCUMENTS

| | | |
|---|---|---|
| EP | 0357270 B1 | 3/1990 |
| EP | 0470912 B1 | 2/1992 |
| EP | 1149582 A2 | 10/2002 |
| EP | 1149562 A3 | 1/2003 |
| GB | 2372707 A | 9/2002 |
| WO | WO03/065906 A2 | 1/2003 |
| WO | WO03/057049 A1 | 7/2003 |

OTHER PUBLICATIONS

Precimed tool advertisement (2002).

Minimally Invasive Hip Surgery and Future Developments. From www.essexhipsurgeon.co.uk/minimally_Invasive_hip-replacement.surgery.html (2003).

Innomed MIS catalog (2003).

McTighe, A New Era of Minimally Invasive Surgical Approaches for THA, Joint Implant Surgery & Research Foundation Update (Dec. 2002).

Berry, et al., Symposium on Minimally Invasive THA, J. Bone Joint Surg. 85A: 2235-2246 (2003).

Pellegrini, et al., Surgical Approaches to the Hip Joint. In: Surgery of the Musculoskeletal System (CM Evarts, Ed.) Churchill Livingstone (New York, NY) Chapter 94, pp. 2735-2756 (1990).

Murphy, Minimally Invasive Hip Surgery, From www.stephensmurphy.com (2003).

\* cited by examiner

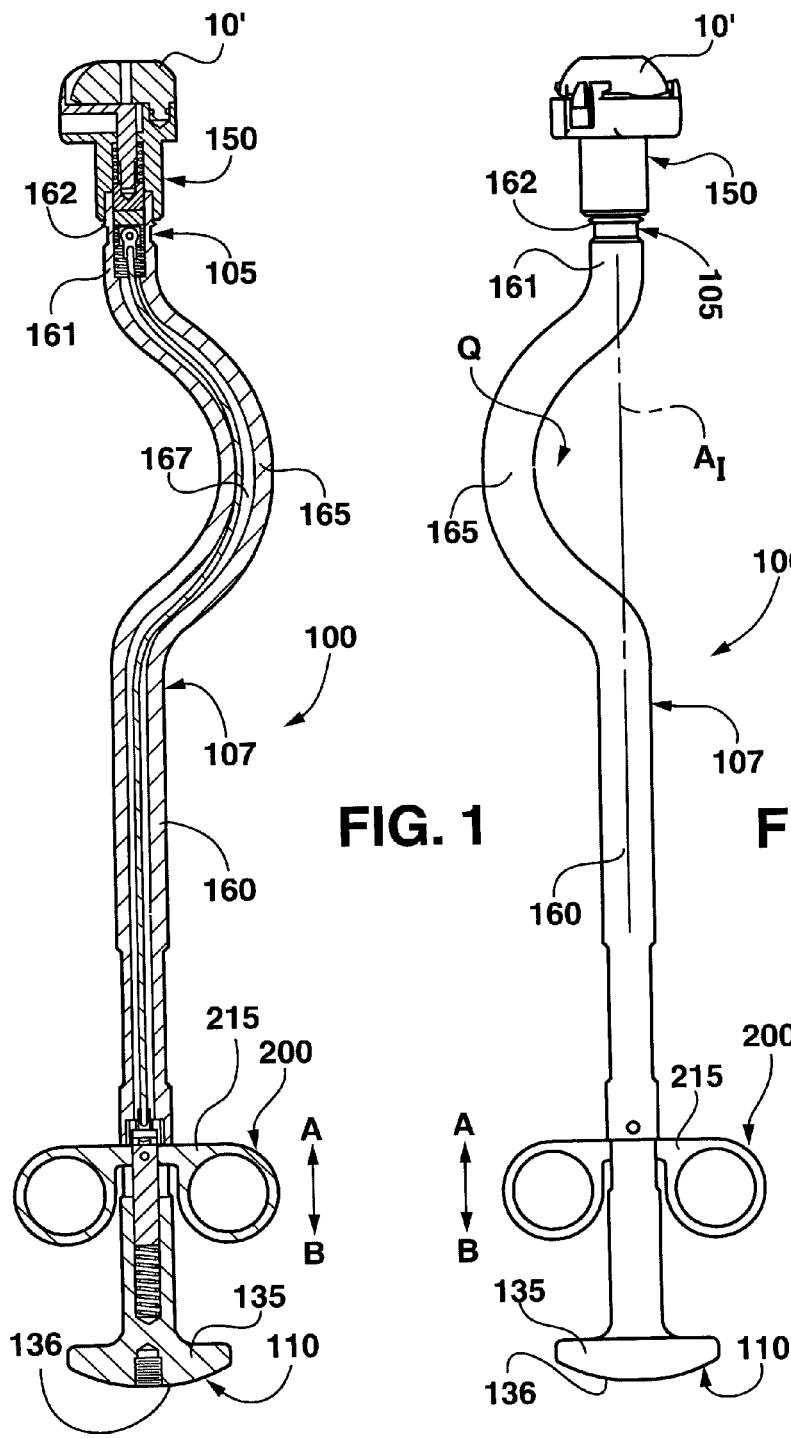

ACETABULAR IMPACTOR

RELATED APPLICATIONS

This application is related to assignee's now abandoned U.S. Provisional Patent Application Ser. No. 60/444,689, filed Feb. 4, 2003.

FIELD OF THE INVENTION

This invention is generally directed to the field of hip arthroplasty. The invention is specifically directed to an improved acetabular impactor, especially suitable for use in minimally invasive hip surgeries.

BACKGROUND OF THE INVENTION

Traditionally, hip replacement surgery has been done via "open" surgical procedures. With open procedures, space for inserting and manipulating surgical instruments is not that critical and it is easier to get around major anatomical features, such as the greater trochanter of the femur.

However, with the advent of minimally-invasive surgical procedures for hip replacement, small incision sizes combined with tight anatomical clearances have resulted in the need for surgical instruments that take maximum availability of available space.

Exemplary instruments specifically described as being designed for MIS surgeries are shown in, for example, U.S. Pub. 2003/0050645 (Parker et al), U.S. Pub. 2003/0158559 (Diaz), and WO03/065906 (Chana). Another device that appears to be at least designed with an eye towards MIS issues is shown in U.S. Pat. No. 5,474,560 (Rohr). However, as shown in Rohr's drawings, its bulging arcuate portion 16 does not seem to extend far enough out to provide a good working clearance for the greater trochanter.

All patents and publications mentioned herein are incorporated by reference in this patent application.

While these devices may be acceptable for their intended or described uses, they are often complex, not geometrically or spatially optimized, not provide for easy one-handed operation, nor provide for the ability to easily handle different sized acetabular shells.

Accordingly, there is room for improvement within the art.

SUMMARY OF THE INVENTION

It is an object of the invention to provide an improved acetabular impactor.

It is an object of the invention to provide an improved acetabular impactor especially suitable for use in minimally invasive surgical procedures.

It is an object of the invention to provide an improved acetabular impactor that is simple in design and operation.

It is an object of the invention to provide an improved acetabular impactor that is spatially optimized.

It is an object of the invention to provide an improved acetabular impactor that provides for easy one-handed operation.

It is an object of the invention to provide an improved acetabular impactor that has the ability to easily handle different sized acetabular shells.

These and other objects of the invention are achieved by an acetabular shell impactor, comprising: an elongated impactor body having impacting and attachment ends; a releasable connection for attaching an acetabular shell to the impactor at the attachment end; an actuator for releasing the connection between the shell and the impactor; and the actuator manipulated at the impacting end.

These and other objects of the invention are achieved by an acetabular shell impactor, comprising: an elongated impactor body having impacting and attachment ends; a releasable connection for attaching an acetabular shell to the impactor at the attachment end; an actuator for releasing the connection between the shell and the impactor; and the actuator manipulated by translation along the longitudinal axis of the impactor body.

These and other objects of the invention are achieved by an acetabular shell impactor, comprising: an elongated impactor body having impacting and attachment ends; a releasable connection for attaching an acetabular shell to the impactor at the attachment end, wherein the releasable connection can be removed from the attachment end of the impactor body to be replaced with a different size releasable connection; an actuator for releasing the connection between the shell and the impactor.

These and other objects of the invention are achieved by an acetabular shell impactor, comprising: an elongated impactor body having impacting and attachment ends, the impacting end including an impacting body having a hole passing there through; a releasable connection for attaching an acetabular shell to the impactor at the attachment end; and an actuator for releasing the connection between the shell and the impactor, the actuator passing through the hole in the impacting body.

These and other objects of the invention are achieved by an acetabular shell impactor, comprising: an elongated impactor body having impacting and attachment ends; a releasable connection for attaching an acetabular shell to the impactor at the attachment end, the releasable connection including a spring; an actuator for releasing the connection between the shell and the impactor, the actuator including a spring; the biasing action of the actuator spring exceeds the biasing action of the releasable connection spring.

BRIEF DESCRIPTION OF THE DRAWINGS

FIG. 1 depicts an exemplary embodiment of an acetabular impactor according to the invention.

FIG. 2 depicts a cross section of the exemplary embodiment of an acetabular impactor according to the invention.

DETAILED DESCRIPTION OF THE DRAWINGS

Figure 3A:
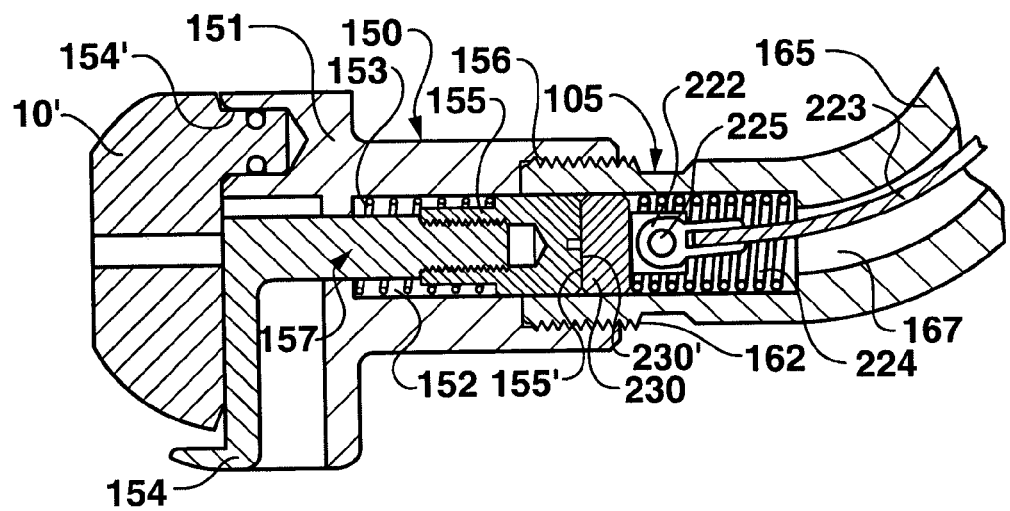
FIG. 3A depicts a cross-section of an exemplary attachment end for use with the exemplary acetabular impactor according to the invention.

With reference to the drawings, various exemplary embodiments of an acetabular impactor that meets and achieves the various objects of the invention set forth above will now be described.

FIG. 1 depicts an exemplary embodiment of an acetabular impactor according to the invention. The acetabular impactor is especially suitable for use in minimally invasive surgery ("MIS"). During MIS, typically an incision size of less than 8 cm will be made. Furthermore, if there is no dislocation of the hip joint during the surgery, available space for surgical instruments will be even further limited. During MIS hip procedures, having acetabular reaming and impacting instruments avoid the greater trochanter becomes critical in the tight space available to the surgeon. Finally, having an impactor that can be released from an acetabular shell without the surgeon having to reach into the tight confines of the incision becomes critical.

The exemplary acetabular impactor 100 according to the invention generally comprises first and second opposite ends. The first end comprises an impacting end 110, which will typically be hit by an impacting tool (not shown), such as a mallet or hammer, as described in any of the references previously cited above. The second end comprises an attachment end 105 for attaching a releasable connection 150 for attaching an acetabular shell 10 (FIG. 3B) of a given size over a shell alignment dome 10' (FIGS. 1–3A) and to the acetabular impactor 100. While releasable connection 150 may be permanently fixed to impactor body 107, by having releasable connection 150 be a separate modular element from the impactor body 107, the acetabular impactor 100 according to the preferred embodiment of the invention has the ability to attach different sized releasable connections 150 to the attachment end 105 of the impactor body 107. This renders the preferred embodiment of acetabular impactor 100 substantially more flexible because a surgeon does not always know in advance what size acetabular shell he may need to use until well into surgery.

Impacting end 110 will typically comprise an impacting body 135 having an impacting surface 136 for direct (or indirect) receipt of the blows of the impacting tool. Between attachment end 105 and impacting end 110, is the body 107 of acetabular impactor 100. The body 107 of acetabular impactor 100 generally comprises straight portions 160, 161 and a curved portion 165 and is hollow, having a central channel 167 throughout its length. Straight portions 160, 161 are at least parallel and typically coaxial along the impact axis $A_I$, which is coaxial with the longitudinal axis of the impactor body 107. Open area Q is spatially optimized for fitting in of the greater trochanter and associated muscles, ligament, and other soft tissue of the femur (not shown) during an acetabular impaction.

Adjacent impacting end 110, impactor 100 has a remote actuator 200 for remotely releasing the acetabular shell 10 from the attachment end 105 of acetabular impactor 100. By "remotely", it is meant that the release may be achieved without the surgeon having to reach into the incision site. According to the preferred embodiment of the invention, actuator 200 includes a translatable/slidable trigger 215. Trigger 215 translates within slot 216 in impacting body 135 and in directions A, B parallel to the longitudinal/impact axis $A_I$ of the impactor body 107.

In general, and as will be described in greater detail below, translation of trigger 215 towards impacting end 110 will result in the release of shell 10 from releasable connection 150 and impactor 100 or the ability of impactor 100 to receive a shell 10. On the other hand, release of trigger 215 towards its rest position opposite impacting end 110 results in the attachment of shell 10 to releasable connection 150 and impactor 100.

As previously mentioned, impacting end 110 will typically comprise an impaction body 135 having an impacting surface 136 and a hole, preferably in the form of a slot 216 there through, for receipt of trigger 215 of actuator 200. Impaction body 135 will be sized so as to allow body 135 to be gripped in a surgeon's hand while fingers of that same hand can easily reach trigger 215 without undue stretching or twisting.

Furthermore, impacting body 135 will typically have a hollow channel 220 therein. Within channel 220 is pull rod 217 which is biased away from impacting end 110 by compression spring 221. Trigger 215 is attached to pull rod 217 by, for example, pin 219.

Finally, a cable 223, preferably having eyelets 222 at both ends for added strength, is attached to pull rod 217 by, for example, a pin 225.

Having discussed the structure of the actuating mechanism 200, reference will now be made to the releasable connection 150 and how it is actuated by actuating mechanism 200.

While releasable connection 150 may take any form, in the preferred embodiment of the invention it takes the form of the releasable connection shown in Assignee's Co-pending U.S. Provisional Patent Application Ser. No. 60/444,689, filed Feb. 4, 2003, and incorporated by reference herein.

Releasable connection 150 is modified from that shown in the previously mentioned provisional patent application primarily as follows. Generally, the actuating sleeve of the provisional application referred to above that is used to raise and lower the locking fingers is replaced with an internal mechanism actuated by piston 230 and spring 224 and their associated structures. Indeed, regardless of the form of the releasable connection 150 selected, it will be modified to be actuated by piston 230 and spring 224 and their associated structures.

As shown in FIG. 3A, releasable connection 150 generally comprises a main body 151 having and alignment dome 10' (e.g. FIG. 3A) and a channel 152 passing there through. Channel 152 has threads 156 for connection to corresponding threads 162 on attachment end 105 of impactor body 107. However, any means of connection may be used and as previously mentioned, the releasable connection 150 may even be permanently attached to the impactor body 107 if acetabular shell size flexibility is not desired. However, it will typically be desired for releasable connection 150 to be a separate modular element from impactor body 107. Within channel 152 is compression spring 153 and piston 155 having a face 155'. Locking member 157 (see locking member 32 of Assignee's co-pending provisional patent application referred to above) is attached to piston 155 for movement therewith and has locking fingers 154. Main body 151 has corresponding locking feet 154', which together with locking fingers 154 act to lock and/or release acetabular shell 10 from releasable connection 150. In the preferred embodiment, when a modular releasable connection 150 is separated from impactor body 107, in its rest state, locking member 157 and its locking fingers 154 are in their retracted position (i.e., FIG. 3B).

As also shown in FIG. 3A, the attachment end 105 of the impactor body has a piston 230 in channel 167. Piston 230 is attached to cable 223 by eyelet 222 and pin 225. Furthermore, compression spring 224 biases piston 230 towards attachment end 105. However, piston 230 cannot fall out of channel 167 because it is retained in position by the interaction of cable 223 and actuator 200, which limits how far it can move. Furthermore, the action of spring 224 generally results in keeping cable 223 taught and trigger 215 in the rest position. If cable 223 becomes slack, the action of spring 221 prevents the rattling of trigger 215 by biasing trigger 215 away from the impacting end 110 and holding trigger 215 flush with face 160' of straight portion 160 of impactor body 107.

Figure 3B:
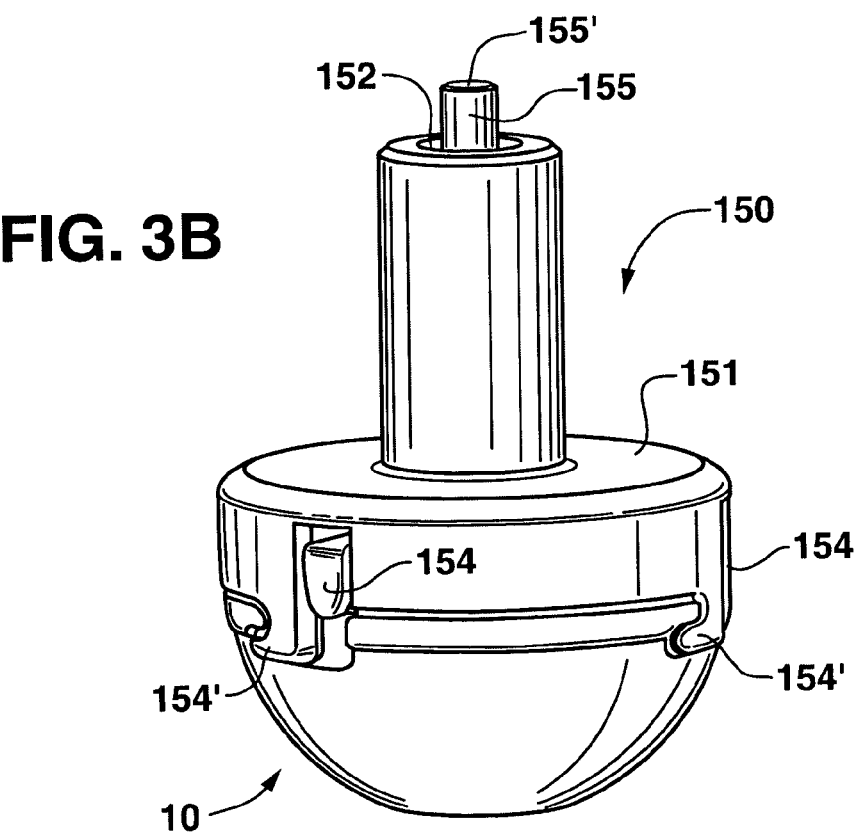
FIG. 3B depicts a perspective view of an exemplary attachment end for use with the exemplary acetabular impactor according to the invention.
Figure 4:
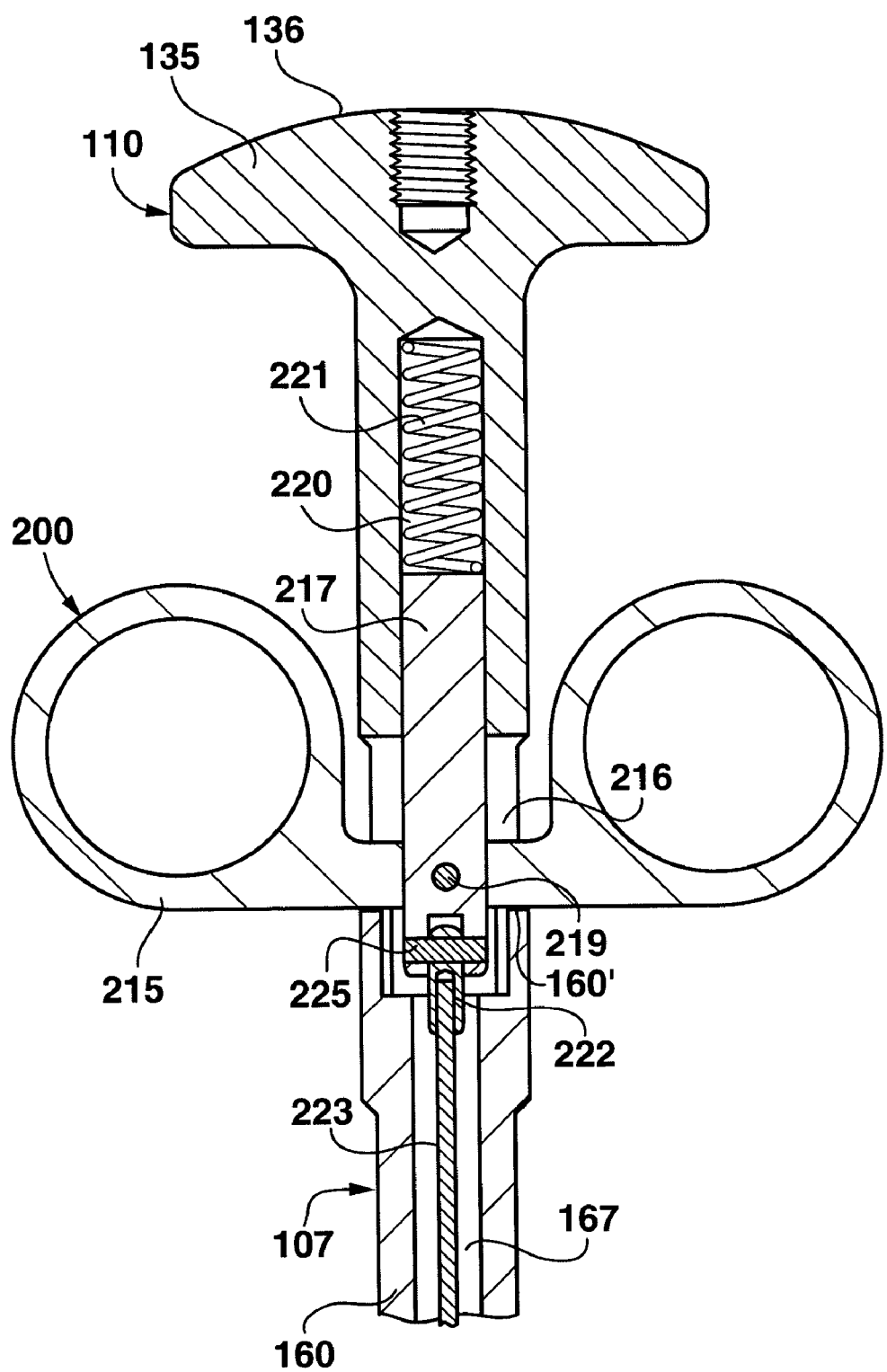
FIG. 4 depicts a cross-section of an exemplary impacting end for use with the exemplary acetabular impactor according to the invention.

When main body 151 of releasable connection 150 is attached to attachment end 105 of impactor body 107, face 155' of piston 155 is brought into contact with face 230' of piston 230. Because spring 224 will be stiffer than spring 153, this will result in locking member 157 and its locking fingers 154 taking their extended position (i.e., FIG. 3A) in the rest position, which is opposite that shown when releasable connection 150 is separate from impactor body 107 (FIG. 3B).

Having described the structure and basic operation of each of the various subcomponents of impactor 100, its overall operation will now be described.

Figure 5:
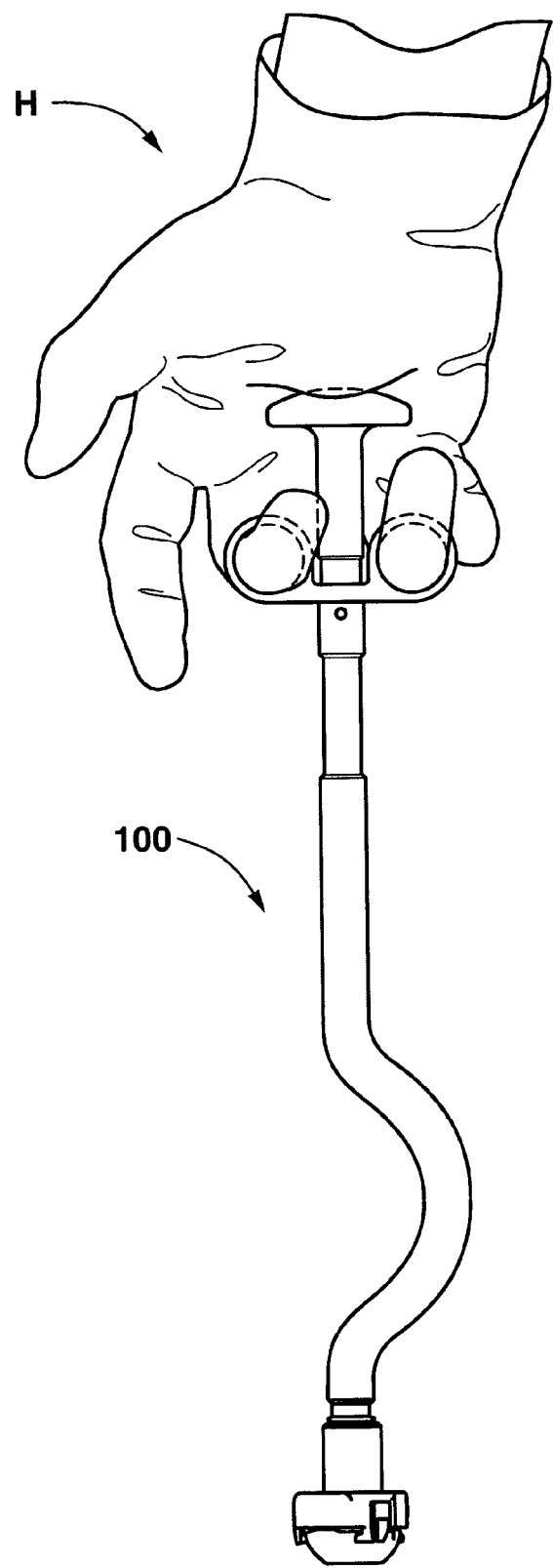
FIG. 5 depicts the exemplary acetabular impactor according to the invention in the hand of a user.

As impactor 100 is designed and intended for one-handed operation, the surgeon will typically pick up impactor 100 by gripping trigger 215 with his fingers and holding impacting end 110 in the same hand H (FIG. 5). Thus, according to the preferred embodiment, actuator 200 is typically manipulated at the impacting end 110. Assuming the impactor 100 is not already attached to an acetabular shell 10, using the same fingers by which he gripped the trigger 215, the surgeon will pull back trigger 215 towards impacting end 110. This results in the movement of pull rod 207 towards impacting end 110 and through pin 225 and eyelet 222, cable 223 is also pulled towards impacting end 110. The pulling on the impacting end of cable 223 results on the pulling on the attachment end of cable 223 and the pulling on the piston 230 further into the attachment end of impactor body 107, against the bias of spring 224. This allows compression spring 153 to push piston 155 towards impacting end 110. As locking member 157 and locking fingers 154 are attached to piston 155, they also move towards impacting end 110 and towards a fully retracted position.

The releasable connection 150 is now ready to receive an acetabular shell 10 and is brought adjacent an acetabular shell 10 to be impacted. Locking feet 154' are brought into alignment with L-shaped recesses 15 in the rim of the acetabular shell 10.

Trigger 215 is then released with the assistance of spring 221. The action of spring 224 results in cable 223 being pulled towards attachment end 105, while allowing piston 230 to move away from impacting end 110. Piston 230 then pushes on piston 155, which ultimately results in locking fingers 154 also being moved into L-shaped recesses 15, thereby locking the acetabular shell 10 to impactor 100.

Impactor 100 is then used like any other conventional impactor to impact the acetabular shell into a prepared acetabulum of a patient. Generally, this involves using an impacting tool (not shown), such as a mallet or hammer, as described in any of the references previously cited above to hit impacting surface 136 and drive the acetabular shell 10 into the prepared acetabulum. Varus and valgus can be adjusted by manipulating the impactor body 107 (such as by angulating) during the impaction process.

After impaction, the process described above to move locking member 157 and locking fingers 154 towards impacting end 110 and towards a fully retracted position is repeated, preferably using one hand and without the surgeon needing to insert any hand in the open incision. As locking fingers 154 are retracted, they exit recesses 15 in acetabular shell 10. This provides room for the removal of locking feet 154' from recesses 15 and the overall separation of impactor 100 from impacted acetabular shell 10.

Acetabular impactor 100 has been so far described above with respect to a non-surgical navigation assisted device. However, it is extremely easy to add navigation markers or other alignment means to any portion of the acetabular impactor, for example, close to the impacting end 110 for use in setting varus, valgus, and leg length with an external camera and navigation system. A detailed description of surgical navigation or the various types of alignment means available are beyond the scope of this application but well known in the art.

While the invention has been described with relation to certain proposed exemplary and preferred embodiments, the invention is not so limited. Reference should be made to the claims when assessing the scope of the true invention.

What is claimed is:

1. An acetabular shell impactor for use in selectively engaging and impacting acetabular shells of different sizes, comprising:

an elongated impactor body having impacting and attachment ends;

a releasable connection for attaching an acetabular shell to said impactor at said attachment end, said releasable connection comprising an alignment dome portion having at least one locking finger thereon, and a releasable connection spring loaded piston member, said releasable connection spring loaded piston neither normally biasing said at least one locking finger into a retracted or unlocked position, said attachment end of said impactor body having an impactor body spring-loaded piston member, said impactor body spring-loaded piston member normally biased into an extended or locked position, said impactor body spring loaded piston member positioned to abut against said releasable connection spring-loaded piston member when said releasable connection is attached to said impactor body, said impactor body spring-loaded piston member having a force greater than that of said releasable connection spring-loaded piston member such that when said releasable connection is attached to said impactor body said impactor body spring-loaded piston member normally biases said at least one locking finger of said releasable connection into said extended or locked position, and said impactor body spring-loaded piston member selectively compressible from said impactor end via an actuator to thereby remotely release said at least one locking finger into the retracted or unlocked position, whereby the acetabular shell can be inserted onto or removed from said releasable connection.

2. The acetabular shell impactor of claim 1, wherein said releasable connection further comprises a plurality of locking feet sized and positioned to fit into corresponding recesses along a rim of the acetabular shell, and said at least one locking finger positioned and configured to selectively lock said locking feet in the recesses of the acetabular shell.

3. The acetabular impactor of claim 2, further comprising said impactor body having a channel extending between said impacting end and said attachment end, and a cable in said channel, said cable operatively linked between said impactor body spring-loaded piston member and said actuator, whereby compression force applied to said actuator at said impaction end causes said cable to translate toward said impaction end and compress said impactor body spring-loaded piston member into a retracted or unlocked position.

4. The acetabular impactor of claim 2, further comprising said impactor body having a curved portion closer to said attachment end than to said impacting end, said curved portion positioned and configured to provide an open area for receiving a greater trochanter of a patient during use of the acetabular shell impactor.

5. The acetabular impactor of claim 4, further comprising said impactor body having a channel extending between said impacting end and said attachment end, and a cable in said channel, said cable operatively linked between said impactor body spring-loaded piston member and said actuator, whereby compression force applied to said actuator at said impaction end causes said cable to translate toward said impaction end and compress said impactor body spring-loaded piston member into a retracted or unlocked position.

6. The acetabular impactor of claim 5, wherein said releasable connection can be removed using screw threads.

7. The acetabular impactor of claim 1, further comprising said impactor body having a curved portion closer to said attachment end than to said impacting end, said curved portion positioned and configured to provide an open area for receiving a greater trochanter of a patient during use of the acetabular shell impactor.

8. The acetabular impactor of claim 7, further comprising said impactor body having a channel extending between said impacting end and said attachment end, and a cable in said channel, said cable operatively linked between said impactor body spring-loaded piston member and said actuator, whereby compression force applied to said actuator at said impaction end causes said cable to translate toward said impaction end and compress said impactor body spring-loaded piston member into a retracted or unlocked position.

9. The acetabular impactor of claim 8, wherein said releasable connection can be removed using screw threads.

10. The acetabular impactor of claim 1, further comprising said impactor body having a channel extending between said impacting end and said attachment end, and a cable in said channel, said cable operatively linked between said impactor body spring-loaded piston member and said actuator, whereby compression force applied to said actuator at said impaction end causes said cable to translate toward said impaction end and compress said impactor body spring-loaded piston member into a retracted or unlocked position.

11. The acetabular impactor of claim 10, wherein said releasable connection can be removed using screw threads.

12. The acetabular shell impactor of claim 11, wherein said releasable connection further comprises a plurality of locking feet sized and positioned to fit into corresponding recesses along a rim of the acetabular shell, and said at least one locking finger positioned and configured to selectively lock said locking feet in the recesses of the acetabular shell.

13. The acetabular impactor of claim 1, wherein said releasable connection can be removed using screw threads.

14. The acetabular shell impactor of claim 13, wherein said releasable connection further comprises a plurality of locking feet sized and positioned to fit into corresponding recesses along a rim of the acetabular shell, and said at least one locking finger positioned and configured to selectively lock said locking feet in the recesses of the acetabular shell.

15. The acetabular impactor of claim 14, further comprising said impactor body having a curved portion closer to said attachment end than to said impacting end, said curved portion positioned and configured to provide an open area for receiving a greater trochanter of a patient during use of the acetabular shell impactor.

16. The acetabular impactor according to claim 1, wherein said actuator is configured for one-handed operation.

17. The acetabular impactor according to claim 16, wherein said actuator is configured for one handed operation by holding the impacting end of said impactor in one hand and using fingers of the same hand to manipulate said actuator.

18. The acetabular impactor according to claim 17, wherein manipulation of said actuator comprises translation along the longitudinal axis of said impactor body.

* * * * *